United States Patent [19]  [11] 4,097,238
Ashley  [45] Jun. 27, 1978

[54] METHOD OF ANALYZING BLOOD PLASMA CLOTTING

[76] Inventor: Sheldon J. Ashley, 147-15 84th Rd., Jamaica, N.Y. 11355

[21] Appl. No.: 803,070

[22] Filed: Jun. 3, 1977

[51] Int. Cl.² ............................................. G01N 33/16
[52] U.S. Cl. ................................. 23/230.3; 23/230 B; 424/1
[58] Field of Search ............... 23/230.3, 230 B; 424/1, 424/11; 73/64.1

[56] References Cited

U.S. PATENT DOCUMENTS

| | | | |
|---|---|---|---|
| 3,458,287 | 7/1969 | Gross et al. | 23/230 B |
| 3,658,480 | 4/1972 | Kane et al. | 23/230 B |
| 3,814,585 | 6/1974 | Bailly | 23/230 B |
| 3,821,643 | 6/1974 | Bostick | 23/230 B |
| 3,854,324 | 12/1974 | Altshuler | 23/230 B |

Primary Examiner—R.E. Serwin
Attorney, Agent, or Firm—Daniel Jay Tick

[57] ABSTRACT

Citrated platelet-rich blood plasma is added to $Tc^{99m}$ macroaggregated albumin or $Tc^{99m}$ human serum albumin microspheres and counted in a well scintillation counter to provide the preclot count. Calcium chloride is added to the combination to initiate the clotting process. An anticoagulant is added to the solution after the formation of a clot to terminate the clot reaction. The residual clot is washed in a normal saline solution. The washed clot is resuspended in a saline solution and is recounted in the well scintillation counter to provide the post-clot count and the clotting time.

8 Claims, 1 Drawing Figure

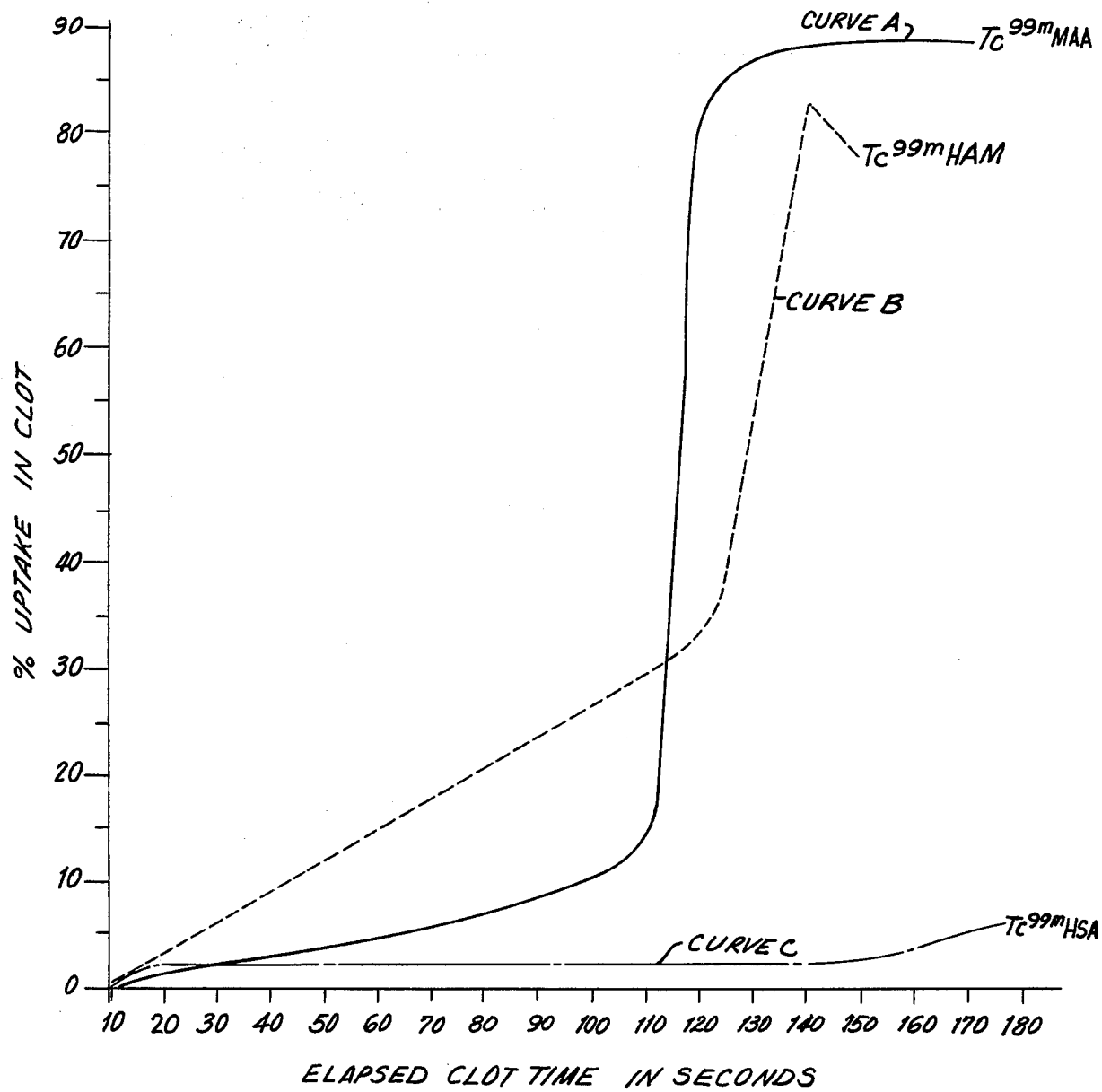

METHOD OF ANALYZING BLOOD PLASMA CLOTTING

BACKGROUND OF THE INVENTION

The present invention relates to a method of analyzing blood plasma clotting.

A known test technique performed by a New Jersey company for determining blood plasma clotting time is known as the Orthodiagnostics Coagulation procedure and is based on the principle that the plasma clotting time is measured by the time for a blood clot to form after the addition of an equal volume of calcium chloride or $CaCl_2$ solution to the plasma. The reproducibility of the test depends upon the centrifugation of the blood samples. Blood plasma rich in platelets clots at a faster rate than plasma poor in platelets.

The reagents used in the known test are $CaCl_2$ and platelet-rich plasma freshly drawn from the subject under normal control.

The blood is drawn into a vacutainer tube containing citrate. The vacutainer tube is then inverted 8 to 10 times to mix properly. The tube is then centrifuged at 2000 rpm in a swing head unit for 5 minutes. The supernate of the platelet-rich plasma is then carefully drawn off by pipetting and placed in a clean empty vacutainer tube.

The known test technique is to pipette 0.3 ml of platelet-rich blood plasma from the subject into a 12 by 75 mm test tube and incubate at 37° C in a water bath for 3 minutes. 0.3 ml of the $CaCl_2$ reagent, at 37° C, is then added to the solution by a blow out technique.

The test tube is kept in the water bath and a stop watch is started when the $CaCl_2$ is added. The tube is gently tilted at 15 second intervals until a clot forms. The stop watch is stopped at the instant the clot is seen and the time is recorded. At least two visual clot times are determined per subject sample to establish the validity of the results. The results are graphed at an arbitrary 50% level on graphs with reference to time, and the clot time is reported as the number of seconds required for the clot to appear.

A normal blood specimen clots in 90 to 150 seconds.

The principal object of the invention is to provide a method of analyzing blood plasma clotting which provides accurate clotting time and information.

An object of the invention is to provide a method of analyzing blood plasma clotting having few and readily undertaken steps.

Another object of the invention is to provide a method of analyzing blood plasma clotting which utilizes simple and easily handled equipment.

Still another object of the invention is to provide a method of analyzing blood plasma clotting which is highly sensitive and thus provides highly accurate clotting time indications.

Yet another object of the invention is to provide a method of analyzing blood plasma clotting which indicates the clotting time, the amount of clottable protein in a blood sample, the amount of uptake of radioparticulates in clotting plasma over discrete periods of time, the degree of clot lysis, breakdown or dissolution over discrete periods of time, a test for comparing the uptake of various radionuclides into forming clots, and what occurs inside the body to clot localization agents.

BRIEF SUMMARY OF THE INVENTION

Citrated platelet-rich blood plasma is added to $Tc^{99m}$ macroaggregated albumin or $Tc^{99m}$ human serum albumin microspheres and counted in a well scintillation counter to provide the preclot count. Calcium chloride is added to the combination to initiate the clotting process. An anticoagulant is added to the solution after the formation of a clot to terminate the clot reaction. The residual clot is washed in a normal saline solution. The washed clot is resuspended in a saline solution and is recounted in the well scintillation counter to provide the post-clot count and the clotting time.

BRIEF DESCRIPTION OF THE DRAWINGS

In order that the invention may be readily carried into effect, it will now be described with reference to the accompanying drawings, wherein the single FIGURE is a graphical representation of the % uptake of a blood clot, as determined by the method of the invention versus the elapsed clot time.

DETAILED DESCRIPTION OF THE INVENTION

The coagulation of blood may be characterized as the formation of a fibrin clot. This is a dynamic process acting in concert with many factions. I have studied this process via in-vitro testing, using a $Tc^{99m}$ labeled aggregate.

Clotting takes place as a cascading enzymatic process. Each of the plasma coagulation factors could be thought of as existing as a pro-enzyme or catalyst, which is converted to an enzyme during the clotting process. The function of each enzyme formed is to activate the pro-enzyme which succeeds it in the coagulation sequence. Thus, pro-enzyme A is converted to enzyme A, which then catalyzes the conversion of pro-enzyme B to enzyme B, and so on, to the formation of a fibrin clot.

At least 13 factors occurring naturally in blood are responsible for clotting. The three main phases of clotting and the time interval over which they occur are the formation of thromboplastic activity in 1 to 3 minutes, followed by the conversion of pro-thrombin to thrombin in 8 to 15 seconds, and finally the conversion of fibrinogen to fibrin in less than 1 second.

Nearly all coagulation tests use the appearance of a fibrin clot as the end point. In considering the use of this end point, it is important to realize that the concern should be with the appearance of a visible clot. At present, the coagulation time is a qualitative observation of fibrin clot formation.

Quantification of the coagulation process is accomplished in the method of the invention by using a radioactive uptake principle. Radioparticulates have an affinity or, at any rate, are readily incorporated into clotting blood. The most dramatic representation of this is the case in which blood incubates in a syringe containing particulate lung material, and, after subsequent injection, radioactive emboli are seen lodged in the capillary bed of the lungs.

It appears that the fibrin clot mechanism is analagous to the formation of a thickening gelatin. Blood passes from a liquid state through which particulate matter may flow freely, to a fibrinous, filamentous network, or gel, generally recognized as a fibrin clot.

As this dynamic process is taking place, particulate material passes less freely through the medium and becomes trapped. In the final stages, it is mechanically and irreversibly bound onto the fibrinous gel, as are red blood cells and platelets.

Platelet-rich plasma contains all the coagulation factors necessary for clotting, with the exception of calcium ions. These are added as a separate step during the test. The rate of clotting is a measure of the overall coagulant activity developed.

In the method of the invention, freshly drawn citrated blood is centrifuged and the platelet-rich plasma supernate is divided into many aliquots. The aliquots, along with measured amounts of $Tc^{99m}$ tagged particulates, are added to vials and counted in a gamma well scintillation detector. This represents the pre-clot count. The clot reaction is initiated in one vial at a time by the addition of calcium chloride solution. For each vial, there is a selected elapsed time at which the clot reaction is terminated by the addition of an anticoagulant such as, for example, Heparin. Each residual clot is retrieved on a wire loop, and is washed in normal saline solution. Once washed, the clot is resuspended in saline solution and is recounted in the well scintillation detector. This is recorded as the post-clot count. The percent uptake of radionuclide onto the forming clot for its elapsed time is derived from the mathematical combination of the pre-clot and the post-clot counts. This procedure is repeated sequentially for longer elapsed times, until the whole clotting process is covered.

Each test determination of an aliquot quantitatively assays the amount of tracer remaining on the clot. This value is expressed as a fraction of the total amount of tracer to which the clot is exposed. These individual tests generate data points which are then plotted on linear graph paper to demonstrate the characteristic clot curves for each of the materials studied.

The three radiotechnetium labeled materials tested were:
1. $Tc^{99m}$ macroaggregated albumin or (MAA)
2. $Tc^{99m}$ human albumin microspheres or (HAM)
3. $Tc^{99m}$ human serum albumin or (HSA)

The labeled (HSA) human serum albumin shows a lack of uptake, less than 5% for all elapsed times. This is of marked importance because it is not a particulate, yet it is composed of the same basic ingredients as the other two materials tested. This serves as the experiments control, to show that clot uptake of particulate material is a legitimate mechanical function.

Human serum albumin microspheres are relatively hard, smooth, spherical particles, having a narrow size distribution of 15 to 45 microns. $Tc^{99m}$ human albumin microspheres or (HAM) are not taken up in forming clots, until an elapsed time of 100 seconds. Over the next 20 seconds, however, microsphere uptake reaches a peak value of 75%.

Human serum albumin macroaggregates are comparatively soft, irregular in shape, and have jagged edges. These particles have a size distribution of 10 to 90 microns. $Tc^{99m}$ macroaggregated albumin particles are not taken up in forming clots, until an elapsed time of 115 seconds. Then, within the next second, an uptake value of 94% is reached. Over extended elapsed clot times, a saturation value of 99% is achieved. $Tc^{99m}$ (MAA) measures the time it takes for the third phase of coagulation to occur, in which fibrinogen is converted to fibrin in less than 1 second. Furthermore, tagged macroaggregated albumin or (MAA) is more intensely bound onto forming clots, and subsequently has higher uptake values than labeled human albumin microspheres. It appears that particle size, shape, and hardness are among the prime factors responsible for radioparticulate entrapment in forming clots. The extent to which each of these variables is significant should be determined by further research.

Although radiolabeled particle entrapment is a controversial subject, thrombus detection procedures are increasingly in use, such as, for example, in radionuclide venography, when the physician is looking for venous occlusion, collateral circulation and other blood flow anomalies, or in peripheral vascular clot localization where the primary concern is thrombus uptake of the radiopharmaceuticals. The test may provide specific information about both hemorrhagic disorders and diffuse intravascular clotting. The test may also better determine Heparin or anticoagulant therapy results and may be used to monitor clot lysis and dissolution.

A practical application of the method of the invention is to quantitate the affinity, specificity, and rate of uptake for presently used clot seeking agents. Formulation of new radiopharmaceuticals may also find the method of the invention a tool of great value.

The following words and phrases, appearing in the disclosure of my invention, are understood to have the following definitions.

aggregates — a solution of particulates aliquots — known measured parts of a whole or large sample blow out technique — the last drop from a volumetric delivery device is forced out and into the receptacle citrate — an anticoagulant fibrin — a naturally occurring clot factor occurring in the body. It is the end product of fibrinogen.

fibrinogen — a naturally occurring clot factor in the body converted to fibrin gamma well scintillation detector — apparatus which counts and measures the amount of radioactivity in test tube samples Heparin — beef lung, 1000 units/ml human albumin — biologic material, component of blood microspheres or HAM — particulate material of a specific size human serum albumin or HSA — particulate material of a different size in-vitro testing — laboratory tests performed in test tubes macroaggregated albumin or MAA — particulate material of a different size particulates — large particles of human serum albumin particulate lung material — a type of radioparticulate injected into a patient usually to obtain pictures of the lungs pipetting — drawing up of a specific volume of fluid and then delivering it into a tube or receptacle by means of a volumetric tube or device platelet — a component of blood concerned with clotting radionuclide — radioactive material radioparticulate — radioactive tagged particulate supernate — the lighter weight portion of a material which is on top of a fluid when it is centrifuged swing head unit — a type of centrifuge where the samples swing out to a 90° angle when spun down $Tc^{99m}$ or $^{99m}Tc$ — radioactive isotope called Technetium 99m thromboplastic — initiation of part of the clotting process by disruption of the tissues tracer — a radioactive material in small amounts uptake rate — rate of incorporation of the radioactive material into another material vacutainer tube — a commercially available unit used to draw blood into tubes which can contain any type of chemicals venography — pictures of the veins and circulation in the feet The method of the invention provides a radioactive clotting time indication for blood plasma. The first step of the method of the invention is to pipette 0.1 ml of a radionuclide into a 12 by 75 mm test tube. 0.3 ml of platlet rich plasma from the subject is added to the radionuclide and the solution is swirled. The swirled solution is incubated in a water bath at 37° C for three minutes. 0.3 ml of $CaCl_2$ reagent is added to the swirled solution in the tube via a blow out technique.

A stop watch is started when the $CaCl_2$ is added. The tube is kept in the 37° C water bath until a clot is formed and is gently tilted every 15 seconds.

After a predetermined time after which a clot may have formed, 0.3 ml of Heparin is added to the solution and the solution is swirled gently. The Heparin is added slowly and with a minimum of turbulence. If this is not done, the forming clot is destroyed and will not retract. When the Heparin is added, the total clotting process ceases and no further radionuclide uptake occurs.

The solution in the tube is left standing for 10 minutes to permit total clot retraction and the settling of fibrin strands. There seems to be a greatly accelerated and obvious clot retraction occurring when the Heparin is added, although Heparin does not lyse clots.

The formed clot, or any fibrin strands which can be accumulated, are then removed by a wire loop. The greatest danger of error or difficulty arises at this stage of the method. In the earlier stages of clot formation, there are many free floating fibrin strands in solution, and such strands cannot always be scooped into the wire loop. The greatest lack of reproducibility occurs at this point, as indicated in prepared graphs of the clotting process over varying periods of time. This problem does not arise in the later stages of clot formation, since even if there are disassociated fibrin strands floating in the solution, they are sticky in nature and readily adhere to the wire loop.

The fibrin strands removed with the wire loop and forming clot are resuspended in saline and are then counted in a gamma well scintillation detector or counter for one minute or to 10,000 counts. If 10,000 counts or more occur in a minute, the counting time is a minute. If less than 10,000 counts are accumulated in a minute, the count continues until 10,000 counts are accumulated. The total number of counts accumulated divided by the number of minutes the sample is counted equals the counts per minute or CPM. What is counted is the clot which has taken up the radioparticulate. Each count is one ionizing event detected by the scintillation counter. The total volume counted is 1.0 ml.

The clot is washed three times with copious amounts of additive free saline solution of 0.9% normal saline solution in 1% Heparin. The same problem arises at this step as in the previous step. Washing is easier and is performed with greater accuracy in the later clotting steps.

The clot is then transferred to a clean 12 by 75mm test tube and is resuspended in 1.0 ml of additive free saline solution which is 0.9% of normal saline solution.

The radioactivity of the clot which has taken up radioparticulates is then counted in a well scintillation detector or well crystal gamma counter for 1 minute or to 10,000 counts.

A one minute background count of the natural radioactivity in the room is taken of 1.0 ml of water in a 12 by 75mm test tube, to establish a background level.

All counts are converted to counts per minute if they are for a longer period than 1 minute.

The original test tube solution then becomes the standard and the residual clot becomes the unknown sample. The background count is subtracted from each of the standard solution and the sample solution counts, so that the residual count is the net count rate.

The % uptake in the forming clot is then calculated by the equation $$\frac{\text{Counts per minute of the sample}}{\text{Counts per minute of the standard}} \times 100.$$

This equation provides a value which is the % uptake in the clot for its elapsed clot time. The clotting time is determined from the % uptake in the count by noting the point in time when the uptake level of the clot reaches an extraordinarily high level as compared to preceding values usually equal to, or greater than, 85 to 90%.

The counting of the standard solution and the counting of the sample solution are performed within fifteen minutes of each other, so that decay due to natural phenomena is negligible. There is thus no need for the introduction of a special decay factor into the equation.

In the FIGURE, the abscissa represents the elapsed clot time in seconds and the ordinate represents the % uptake in the clot. The curves of the FIGURE thus provide an in-vitro plasma clot uptake analysis. Curve A is for the $Tc^{99m}$ macroaggregated albumin or MAA particulate material. Curve B is for the $Tc^{99m}$ human albumin microspheres or HAM particulate material. Curve C is for the $Tc^{99m}$ human serum albumin or $Tc^{99m}$ (HSA). The clot time is readily determined from the graphs of the FIGURE.

The uptake values shown in the FIGURE, indicate a region of low uptake early in the test, followed by a short period of rapidly increased uptake, until a level of saturation is reached. The characteristic uptake patterns of the two materials $Tc^{99m}$(MAA) and $Tc^{99m}$(HAM) are considerably different. The material $Tc^{99m}$ (MAA) shows a greater affinity for forming plasma clots.

The method of the invention indicates a radionuclide uptake principle which may be used to describe the clotting process. There are three phases of uptake in a clot and $Tc^{99m}$ (MAA) is irreversibly trapped and has a greater affinity for forming plasma clots.

The method of the invention may be used to evaluate new clot seeking agents in the laboratory to observe how they will behave in the body, since the method reflects what happens inside the body to clot localization agents. The method of the invention may also be used to differentiate which clot seeking agents may be used to find preformed or forming blood clots in the body.

The method of the invention is usable to indicate specific particulates which, if they go to blood clots, may carry protelytic agents with them to provide a therapeutic value. The method of the invention is also usable to selectively eliminate different clotting factors and to trace the exact step of the clotting mechanism or an inability of the isolated clot factor to react properly in the clotting process.

The radionuclide clot method of the invention indicates an acceleration compared to the observed visual clot times. The method of the invention provides considerably greater sensitivity in attained results, and leads to a quantitative clotting time indicating a method which is very accurate.

As shown in the FIGURE, the $Tc^{99m}$ (MAA) indicates a definite trend in which there is relatively little clot incorporation of radionuclide over intervals of time. Then, at some point in time, there is an enormous amount of the radionuclide incorporated into the forming clot. This may only be brought down to within 2 seconds due to the limitations of manual procedures. Once this step occurs, the clot tends to be saturated out at this point with little increase as time passes.

The $Tc^{99m}$ (HAM) differs from the $Tc^{99m}$ (MAA) since there seems to be a slightly accelerated incorporation of radionuclide into the forming clot, but not nearly as intense. The $Tc^{99m}$ (HAM) continues to have a more gradual increasing uptake slope, compared to the $Tc^{99m}$ (MAA), and tends to saturate out at a lesser uptake as time passes. The $Tc^{99m}$ (HAM) then becomes less over extended intervals of time.

The $Tc^{99m}$ (HSA) has little uptake over any period of time and establishes a control for the procedure which demonstrates that the albumin fraction of the particulates is not the determining factor in the results of the method of the invention, as shown by the curve C of the FIGURE.

The overall results of the method of the invention indicate that $Tc^{99m}$ (MAA) would be the better material to use in attempting to tag in-vitro or in-vivo forming clots due to the apparently greater affinity it has for a forming clot over $Tc^{99m}$ (HAM).

The method of the invention opens new areas for further investigation. Among these are the performance of a variety of tests for clot tagging in-vitro, utilizing radioactive forms of streptokinase, urokinase and fibrinogen procedures, to compare results. If there is a correlation in the results, this may well provide an in-vitro test which may be easily performed to establish the quality of the materials as different batches are made and evaluated for in-vivo use. Differentiation may eventually become possible for determining the better material to use when attempting to tag forming or preformed clots in-vitro or in-vivo.

While the invention has been described by means of a specific example and in a specific embodiment, I do not wish to be limited thereto, for obvious modifications will occur to those skilled in the art without departing from the spirit and scope of the invention.

I claim:

1. A method of analyzing blood plasma clotting, comprising the steps of
    citrating platelet-rich blood plasma;
    adding a $Tc^{99m}$ tagged particulate to the plasma;
    counting the radioactivity of an aliquot of the citrated plasma with added particulate thereby providing the pre-clot count;
    adding calcium chloride solution to initiate the clotting process;
    adding an anticoagulant to the solution after the formation of a clot to terminate the clot reaction;
    washing the residual clot in a normal saline solution;
    resuspending the washed clot in a saline solution; and
    recounting the radioactivity of the resuspended clot to provide the post-clot count and the clotting time.

2. A method as claimed in claim 1, wherein the particulate is $Tc^{99m}$ human albumin microspheres.

3. A method as claimed in claim 1, wherein the particulate is $Tc^{99m}$ macroaggregated albumin.

4. A method as claimed in claim 1, wherein the particulate is $Tc^{99m}$ human serum albumin.

5. A method of analyzing blood plasma clotting, comprising the steps of
    adding platelet-rich plasma to a radionuclide to form a solution;
    swirling the solution;
    incubating the swirled solution in a water bath at a predetermined temperature for a predetermined period of time;
    adding calcium chloride reagent to the swirled solution;
    gently tilting the solution periodically while it is in the bath;
    adding Heparin at a predetermined period of time after the adding of the calcium chloride reagent, slowly and with a minimum turbulence;
    permitting the solution to stand for a predetermined period of time to permit the total clot retraction and the settling of fibrin strands;
    counting the radioactivity of the retrieved clot for a predetermined period of time;
    removing the formed clot and any accumulated fibrin strands;
    washing the clot with copious amounts of additive free saline solution;
    resuspending the washed clot in additive free saline solution;
    counting the radioactivity of the residual clot in a saline solution;
    establishing a background level of the radioactive count of water; and
    determining the % uptake by utilizing the original solution as a standard and the residual clot as the unknown sample thereby to provide an indication of the clotting time.

6. A method as claimed in claim 5, wherein 0.3 ml of platelet-rich plasma is added to 0.1 ml of radionuclide and the swirled solution is incubated in a water bath at 37° C for three minutes.

7. A method as claimed in claim 6, wherein 0.3 ml of calcium chloride is added to the swirled solution, the solution is gently tilted every 15 seconds and 0.3 ml of Heparin is added to the solution.

8. A method as claimed in claim 7, wherein the solution is permitted to stand for 10 minutes, the radionuclide uptake of the clot is counted for one minute and the additive free saline solution is 0.9% normal saline solution in 1% Heparin.

* * * * *